US011986279B2

(12) United States Patent
Soni et al.

(10) Patent No.: US 11,986,279 B2
(45) Date of Patent: May 21, 2024

(54) WEARABLE HEART RATE MONITORING DEVICE FOR INFANTS

(71) Applicants: Aneesh Soni, Suffern, NY (US); Zarif Choudhury, New York, NY (US); Aashima Garg, San Francisco, CA (US); Abhishek Ramani, Grapevine, TX (US); Ejeh Okorafor, San Diego, CA (US); Justin Hoang, Arlington, TX (US)

(72) Inventors: Aneesh Soni, Suffern, NY (US); Zarif Choudhury, New York, NY (US); Aashima Garg, San Francisco, CA (US); Abhishek Ramani, Grapevine, TX (US); Ejeh Okorafor, San Diego, CA (US); Justin Hoang, Arlington, TX (US)

( * ) Notice: Subject to any disclaimer, the term of this patent is extended or adjusted under 35 U.S.C. 154(b) by 228 days.

(21) Appl. No.: 17/180,460

(22) Filed: Feb. 19, 2021

(65) Prior Publication Data

US 2021/0330198 A1    Oct. 28, 2021

Related U.S. Application Data

(60) Provisional application No. 63/014,604, filed on Apr. 23, 2020.

(51) Int. Cl.
*A61B 5/0255* (2006.01)
*A61B 5/00* (2006.01)

(52) U.S. Cl.
CPC .......... *A61B 5/0255* (2013.01); *A61B 5/0004* (2013.01); *A61B 5/6804* (2013.01);
(Continued)

(58) Field of Classification Search
CPC ... A61B 5/0255; A61B 5/0004; A61B 5/6804; A61B 5/7435; A61B 2503/045;
(Continued)

(56) References Cited

U.S. PATENT DOCUMENTS 5,555,891 A * 9/1996 Eisenfeld ............... A61B 5/486
600/595
6,024,575 A * 2/2000 Ulrich .................... A43B 17/00
434/262
(Continued)

FOREIGN PATENT DOCUMENTS

KR    101778637 B1    9/2017
WO    96/38080 A2    12/1996

OTHER PUBLICATIONS

Yang Xu et al; "A Portable Ultrasonic Bone Densitometer for the Measurement of Multiple Sites"; 2019 International Conference on Manufacturing Science and Information Engineering.

*Primary Examiner* — Jonathan T Kuo
(74) *Attorney, Agent, or Firm* — Anila Kethe; Edward D. Pergament; Pergament & Cepeda LLP (57) ABSTRACT

Various embodiments of a method and a device for monitoring the health of an infant are disclosed. A wearable infant monitoring device comprising a sensing module 170 comprising: a heart rate sensor 150 configured to provide output data corresponding to heart rate of the infant wearing the infant monitoring device; a microcontroller 100 configured to receive and transmit output data; a vibration motor 140 configured to vibrate whenever the heart rate of the infant falls below a customized range; a BLE module 110 in operational unity with the microcontroller that transmits heart rate data to a user on an individual computing device application 120; a computer device application configured to receive and process the output data and generate the infant's heart rate. A method of monitoring an infant's heart rate
(Continued)

using the wearable heart rate monitoring device comprising the heart rate sensor 150 collecting output data, wherein the output data provides information about the infant's heart rate; the microcontroller 100 receiving and transmitting the output data to the BLE module; the BLE module 110 transmitting the output data directly to a user computing device application, which computing device application processes the output data and generates the infant heart rate.

15 Claims, 3 Drawing Sheets

(52) U.S. Cl.
CPC ...... *A61B 5/7435* (2013.01); *A61B 2503/045* (2013.01); *A61B 2560/02* (2013.01)

(58) Field of Classification Search
CPC .............. A61B 2560/02; A61B 5/6807; A61B 2503/04; A61B 2562/0204; A61B 5/002; A61B 5/6802; A61B 5/7455; A61B 5/02438; A61B 5/7275
See application file for complete search history.

(56) References Cited

U.S. PATENT DOCUMENTS

| | | | |
|---|---|---|---|
| 8,620,448 B1 | 12/2013 | Delia | |
| 8,821,418 B2 * | 9/2014 | Meger | G16H 50/30 600/595 |
| 8,945,017 B2 | 2/2015 | Venkatraman et al. | |
| 9,188,460 B2 * | 11/2015 | Burton | G06F 17/40 |
| 9,693,730 B2 | 7/2017 | Workman et al. | |
| 9,717,464 B2 | 8/2017 | Frix et al. | |
| 9,955,877 B2 * | 5/2018 | Delia | A61B 5/14551 |
| 10,223,497 B2 | 3/2019 | Pradeep et al. | |
| 10,226,191 B2 | 3/2019 | Kim | |
| 10,463,168 B2 * | 11/2019 | Karp | A47D 15/008 |
| 10,537,403 B2 * | 1/2020 | Vora | A61B 90/98 |
| 10,743,782 B1 | 8/2020 | Mahar | |
| 11,033,206 B2 * | 6/2021 | Roh | A61B 5/0022 |
| 2011/0112442 A1 * | 5/2011 | Meger | A61B 5/4818 600/595 |
| 2014/0035761 A1 * | 2/2014 | Burton | G01D 4/002 340/870.02 |
| 2015/0194031 A1 * | 7/2015 | Cutler | G08B 21/088 340/573.1 |
| 2016/0035205 A1 | 2/2016 | Messenger et al. | |
| 2016/0174728 A1 * | 6/2016 | Karp | A47D 9/02 5/655 |
| 2016/0262637 A1 * | 9/2016 | Delia | A61B 5/02055 |
| 2016/0287073 A1 | 10/2016 | Pradeep et al. | |
| 2016/0287097 A1 | 10/2016 | Pradeep et al. | |
| 2016/0287098 A1 | 10/2016 | Pradeep et al. | |
| 2016/0287185 A1 | 10/2016 | Pradeep et al. | |
| 2016/0292981 A1 | 10/2016 | Pradeep et al. | |
| 2016/0292983 A1 | 10/2016 | Pradeep et al. | |
| 2016/0292986 A1 | 10/2016 | Pradeep et al. | |
| 2016/0293026 A1 | 10/2016 | Pradeep et al. | |
| 2016/0331273 A1 * | 11/2016 | Armoundas | A61B 5/282 |
| 2016/0338798 A1 * | 11/2016 | Vora | A61B 90/98 |
| 2017/0281087 A1 | 10/2017 | Workman et al. | |
| 2017/0347923 A1 * | 12/2017 | Roh | A61F 13/00051 |
| 2018/0096614 A1 | 4/2018 | Pradeep et al. | |
| 2019/0340515 A1 | 11/2019 | Pathak et al. | |
| 2020/0163602 A1 * | 5/2020 | Pareddy | A61B 5/6807 |
| 2020/0334967 A1 * | 10/2020 | Sharma | G08B 21/0453 |

* cited by examiner

FIG. 3

WEARABLE HEART RATE MONITORING DEVICE FOR INFANTS

CROSS-REFERENCE TO RELATED APPLICATIONS

This application claims foreign priority to U.S. Provisional Application Ser. No. 63/014,604 filed on Apr. 23, 2020, which is incorporated herein by reference in its entirety.

FIELD OF THE INVENTION

The present invention is related to a wearable infant monitoring equipment and a corresponding customizable computing device application. More specifically, the present invention is related to a wearable device for monitoring the health of an infant both at home and while outside the home.

BACKGROUND OF THE INVENTION

Sudden Infant Death Syndrome ("SIDS") is the unexplained death of a seemingly healthy baby that occurs while the baby is sleeping. SIDS is a serious problem that is causing the death of thousands of babies every year. Certain physical factors coupled with baby's surroundings increase the risk of SIDS. Since the specific causes of SIDS may be difficult to determine, parents, especially first-time parents, undergo tremendous amount of stress and worry to monitor and ensure the health and well-being of their baby.

In order to help parents, there are various products for monitoring the health of the baby during the crucial first year after birth. Conventional infant monitoring systems include audio or visual monitors that collect aural or visual information and transmit the information to another device that allows a caregiver, such as a parent, to view or hear the information. Essentially, these monitoring systems allow a caregiver to hear or observe the infant from a different room or location. While, this type of monitoring occurs in real-time, a caregiver must infer the health of the baby based on the sounds and sights transmitted through the monitoring systems. Be it a first-time parent or a caregiver with experience, it is extremely difficult to remain alert at all times of the day to watch out for signs that signal distress in the baby. As such, a device that removes this step of inference and is able to convey the health of baby in quantifiable terms such as heart rate, temperature etc., is more valuable than the conventional monitoring devices.

Some wearable devices provide rudimentary heartrate and temperature information about an infant to a caregiver. For example, KR101778637 discloses a wearable device for the infant. Based on the information collected through several types of sensors, such as heart rate, temperature, humidity etc., the device characterizes the need and/or condition of the infant such as hunger, sleep, bowel movement, lactation etc. The device then transmits the data to an external terminal or server that then relays the same information to the caregiver.

U.S. Pat. No. 9,693,730 owned by Owlet Protection Enterprises, discloses a similar system which comprises a wireless infant health monitor comprising a sensing module removably disposed within a wearable article such a foot wrap or sock. The sensing module is provided with sensors that can measure motion data, sleeping data, heart rate, temperature data etc., which data is processed and transmitted to a receiving station. The receiving station further processes the data and displays the data along with historical trend data or sends the same to a server or user.

The above methods and systems along with some other inventions in this technological field are useful to a certain extent. However, they all suffer from having multiple units, often wired, situated in and around the baby's surrounding that are cumbersome to install, maintain, complicated to use, and expensive. US 2016/0287097; US 2016/0287185; US 2016/0287098; US 2016/0292981; US 2016/0292983; US 2016/0292986; US 2016/0293026; U.S. Pat. No. 10,223,497; US 2018/0096614; US 2019/0340515. Some of these systems have many wires and units that parents consider them unsafe and/or unsightly around a baby. US 2016/0035205; KR101778637.

Further, the above systems also require an internet connection via Wi-Fi to be able to monitor the infant over a computing device such as a phone. For example, the device of the US '730 patent described above, requires internet/Wi-Fi to transmit the data from the receiving station to a user. In the absence of internet connection, all notifications will be directed to the receiving station. Thus, effectively, none of these baby monitoring devices may be used to monitor an infant over a phone in places without Wi-Fi/Internet connection. For example, there are currently no solutions for monitoring a baby while the parent is driving him/her to a doctor's office. Similarly, if a new mother is leaving her baby with a babysitter at a place other than her home, she has no other way to monitor the health of the baby than to rely of the information provided by the babysitter. In short, the present state of prior art does not provide an easy to use, economical monitoring of an infant outside the confines of a home.

The present invention solves the issues discussed above by providing a wearable infant monitoring device that may be used—inside and outside the house—to monitor the health of an infant. The present invention is an improvement over the inventions of the prior art in providing a monitoring device that is a single compact unit that directly communicates with a user's computing device over Bluetooth technology without multiple or any intermediary units.

SUMMARY

A wearable infant monitoring device comprising a sensing module 170 which comprises a heart rate sensor 150 configured to provide output data corresponding to the heart rate of an infant wearing the infant monitoring device; a microcontroller 100 configured to receive and transmit output data received from the heart rate sensor; a vibration motor 140 configured to vibrate whenever the heart rate of the infant falls below a pre-customized range; a BLE module 110 in operational unity with the microcontroller that transmits heart rate data to a user on an individual computing device application 120; a computing device application 120 that is configured to receive and process data from the BLE module; wherein the BLE module 110 sends the readings to the user computing device application 120 without an intermediary transmitting unit.

A wearable infant monitoring device as described above, wherein the microcontroller 100 is an Arduino® microcontroller.

A wearable infant monitoring device as described above, further comprising a microphone 180 configured to record the noise of the environment around the baby.

A method of monitoring an infant's heart rate using the wearable heart rate monitoring device as described above, comprising the heart rate sensor 150 collecting output data;

the microcontroller 100 receiving and transmitting the output data to the BLE module; the BLE module 110 transmitting the heart rate directly to a user computing device application 120 which receives and processes the data received and determines the heart rate of the infant.

The method as described above, further comprising: the computing device application 120 detecting an alarming heart rate; triggering a notification regarding the same to alert the user of the phone and also alerting other users connected to the infant profile via their respective computing device applications through cloud technology; wherein the alarming heart rate is any heart rate value that falls outside a pre-customized heart rate range.

The method as described above, further comprising computing device application 120 transmitting instructions to the infant monitor to trigger a response on the vibrational motor 140. The amount of time that the vibrational motor vibrates may be set by the user on the computing device application. For example, the motor may be set to vibrate for 5 min, 4 min, 3 min, 2 min, 1 min or less than or more than any of those periods. The vibrational motor 140 may be silenced by the user from the phone. In such an embodiment, a user may silence the motor by using a "toggle" on the computing device application. In an alternate embodiment, the vibrational motor may be silenced by a physical switch on the infant monitoring device. Both options—silencing the motor by means of a "toggle" on the computing device application of the phone, or silencing the motor manually by means of a physical switch incorporated on the infant monitor, may be present at the same time.

The method as described above, further comprising: the microphone 180 recording output related to noise environment from the infant surroundings; the microcontroller 100 transmitting the output from the microphone to the computing device application; the computing device application receiving and processing the output and detecting a possible "attention-requiring instance"; the computing device application alerting the user of the phone (in accordance with the user's notifications settings) if and when the "attention-requiring instance is detected" and simultaneously also alerting other users connected to the infant profile (in accordance the specific user's notification settings) on their individual computing device applications via cloud technology. The attention-requiring instance according to this embodiment is any instance where the output related to the noise environment is substantially different when compared to a pre-recorded baseline noise environment.

The method of monitoring an infant's heart rate using the wearable heart rate monitoring device, wherein the heart rate readings are accurate to within ±4 BPM.

The method of monitoring an infant's heart rate as described above, wherein the infant monitoring device transmits the heart rate to a primary user in the Bluetooth range of the monitoring device without an internet/Wi-Fi connection.

DETAILED DESCRIPTION

The invention is defined with reference to the appended claims. With respect to the claims, the glossary that follows provides the relevant definitions.

A User according to the invention is a parent, babysitter, caregiver or any person related to the infant who wants to monitor the health status of a baby. The user downloads and installs the computer device application 120 related to the infant baby monitoring device of the present invention on his/her mobile computing device. The mobile computing device according to the invention is a phone or any other device which is Bluetooth enabled, able to connect with wireless internet connections and can download the computer device application of the present invention.

In an embodiment of the invention, according to the level of freedom available to customize various functional settings of the infant monitor through the computing device application, a user is a "controlling user" or a "non-controlling user." There can be one or more controlling users and one or more non-controlling users. For example, in a typical scenario, both parents could be controlling users and their babysitter could be a "non-controlling user." The amount of freedom available for the "non-controlling user" to customize settings on the device is set by the "controlling user(s)." A controlling user(s) could also be a "primary user" or designate another person as a "primary user." A primary user is any user in the Bluetooth range of the infant monitor and could be a controlling, non-controlling or a temporary third party user.

The user according to the invention receives health updates from the infant monitor as long as one primary user's phone is in the Bluetooth range of the infant monitor and is able to transmit the data to other users or to a cloud server. In other words, a user not in the Bluetooth range may also receive the health data from the infant monitor as long as the primary user is in the Bluetooth range.

According to an embodiment of the invention, it is required that at least one primary user stays within the Bluetooth range of the infant monitor in order for other users to receive the heart rate data. In a further embodiment of the invention, the primary user is able to upload the data to a cloud server for the other users (who are not in the Bluetooth network) to receive the heart-rate data. There can be more than one primary users. A primary user may be designated on the Bluetooth application by the "controlling user" and may be changed according to convenience. In other words, the primary user is not necessarily a parent/caretaker but any person available to be present within the Bluetooth range of the infant monitor. For example, it is possible for a parent/caretaker—the controlling user(s)—to designate a phone in their daycare center as the primary phone, on a temporary basis. In such a case, the temporary user may be given freedom to the monitor only to the extent that they are able to record and transmit the heartrate data. That is, grant of any additional authority to the daycare center phone in terms of ability to customize the notification settings, or any other functional settings of the device lies with the controlling users.

Any user allowed by the "controlling user(s)" may receive notifications from the infant monitor. Notifiable users of the present invention are either the network of users connected to a single device or a single child's profile such that they can all receive data once the data has been uploaded by the primary user to the cloud and subsequently downloaded by them from the cloud.

Heart rate according to the invention is the speed of the heartbeat measured by the number of contractions (beats) of the heart per minute (bpm). Heart rate in the present disclosure may also be referred to as 'data' or 'readings' or 'output' or 'output data.' Heart rate data measured by the heart rate sensor 150 is raw data, readings or output or 'output data.' The heart rate data from the microcontroller 100 may either be raw data or processed data that is determined to be a heart rate value. Alternatively, the raw data may be processed by the computer device application. In a preferred embodiment of the invention, the heart rate data is measured by the heart rate sensor 150, transmitted by the microcontroller via the BLE module to the computing device application; the computing device application processes the data and determines the heart rate value. Historical data is data saved from previous recordings in the past hour, day, week, month, and year. Historical data may be saved on the cloud based server. Historical data may be analyzed to observe trends and patterns in the heart rate data by the computer device application 120. Historical data may be displayed as graphs, pie charts or in other visually discernible formats for easy tracking of the infant health.

A wearable article according to the invention is a sock or a wrap that is adapted to house the sensing module 170. The sock can comprise a unique strapping mechanism or stretchable material that wraps around the infant's foot. The upper part of the sock can secure around the infant's ankle. The lower part of the sock can secure around the infant's foot. In at least one embodiment, the straps of the sock can be secured by Velcro. Properly applying the straps of the present invention can create a strapping system that minimizes the infant's ability to kick the sock off.

In one embodiment, the sock can also comprise a pouch configured to receive the sensing module 170. The pouch can comprise a zipper or any similar enclosure that allows the pouch to securely open and close. Additionally, in at least one implementation, the pouch can comprise buttons, Velcro, snaps, or other apparatus or useful combination of apparatuses to close the pouch. Additionally, the wearable article may have, in part, a water-resistant pocket such as silicone or plastic that may be used to house the sensing module 170.

In at least one implementation, the sock is configured for the sensing module 170 to be removed from the sock. One will understand that the ability to remove the sensing module 170 from the sock provides several benefits. For example, a sock can easily be laundered by simply removing the sensing module 170 and washing the sock. Additionally, the same sensing module 170 can be used in socks of different size i.e., by simply removing the sensing module 170 from a sock of a first size and inserting it into a sock of a second size.

Figure 1:
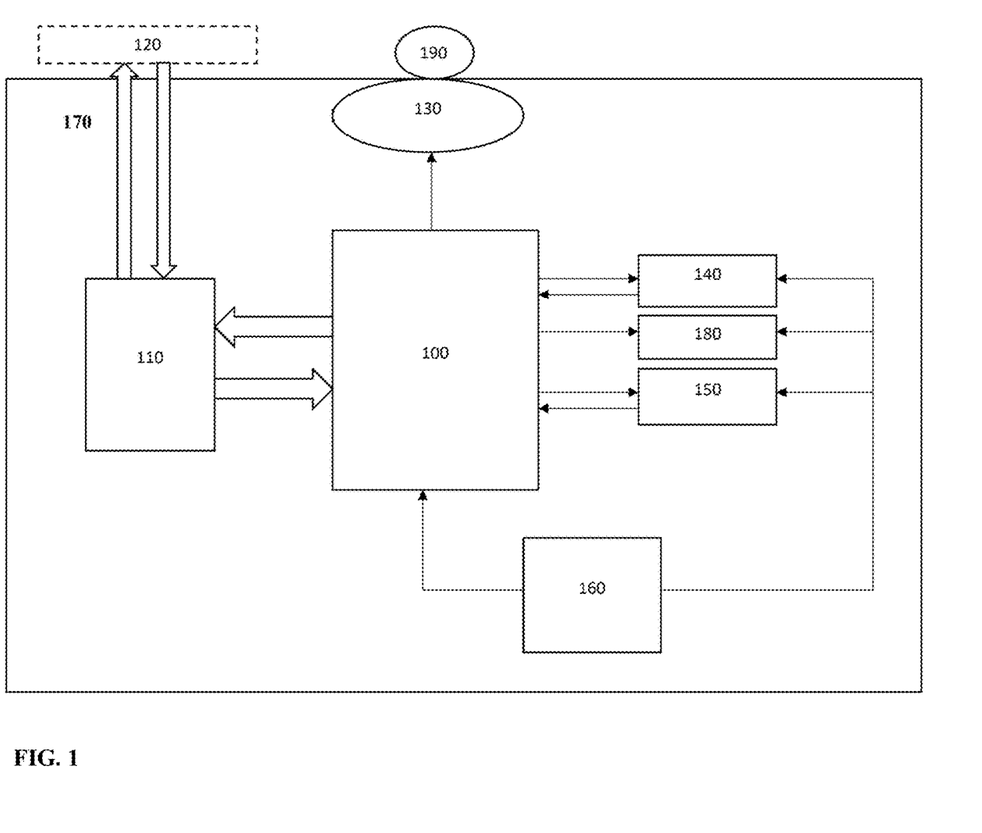
FIG. 1 illustrates the infant heart rate monitor and its components: a Sensing module (170); with heart rate sensor (150); a microcontroller/processing unit (100); a vibration motor (140); a BLE module (110); computing device application (120); Microphone (180); Battery (160); visual indicator (190).
Figure 2:
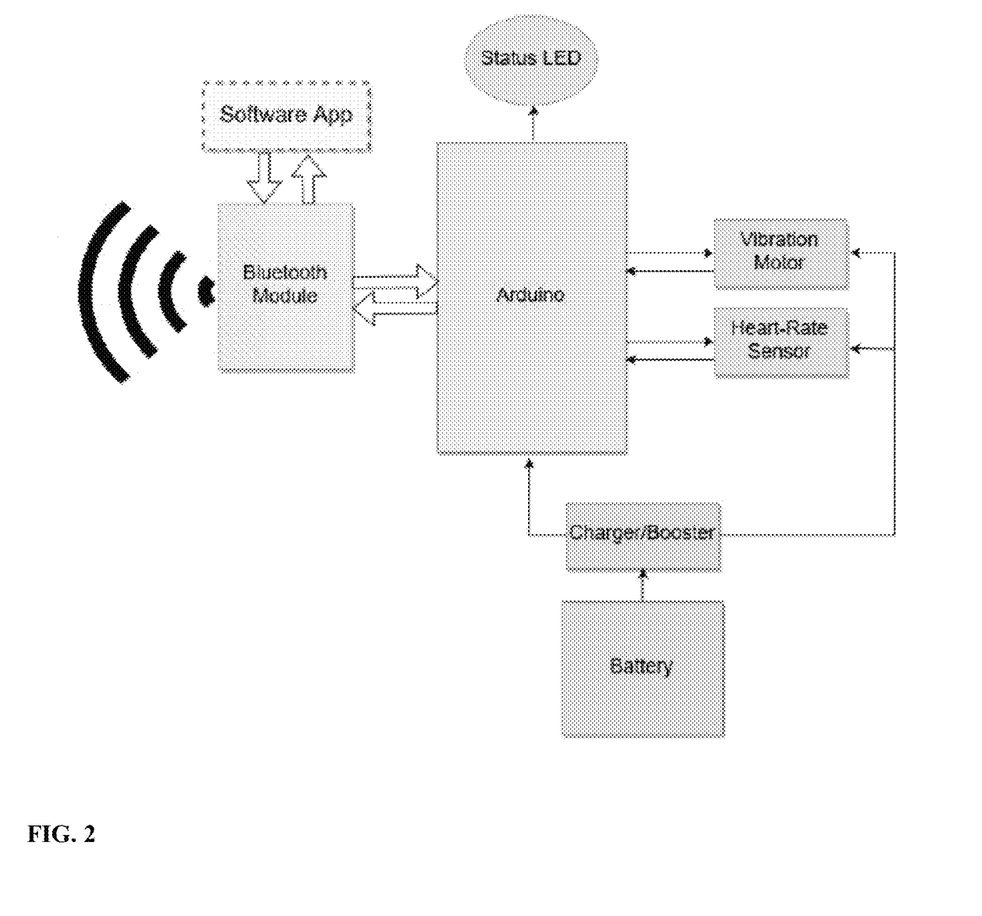
FIG. 2 shows the workflow of the heart rate monitor within its various internal components, as embodied by the present invention.
Figure 3:
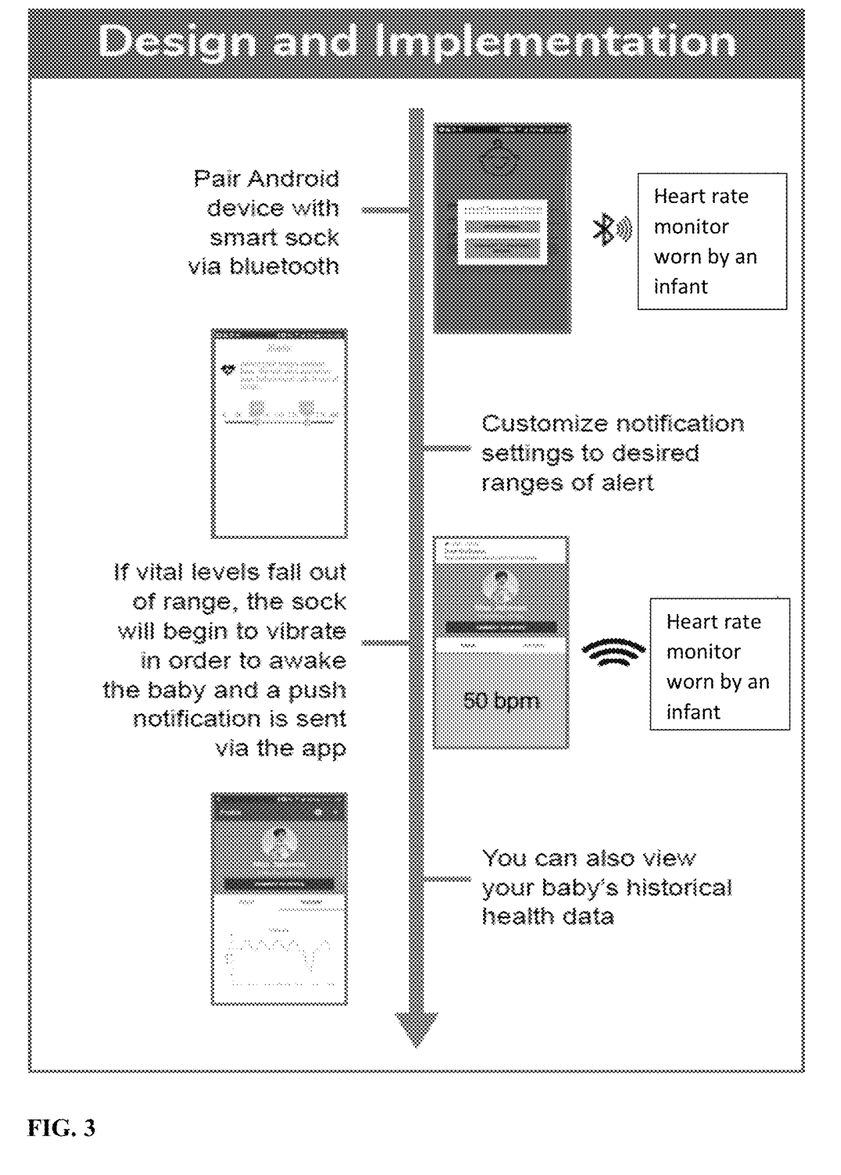
FIG. 3 shows a typical design and implementation embodied by the present invention.

The sensing module 170 according to the invention, as shown in FIG. 1 and FIG. 2 comprises components of the wearable infant heart rate monitor. In an embodiment of the invention, the sensing module 170 comprises of a heart-rate sensor 150; a microcontroller 100; a vibration motor 140; and a BLE module 110. The sensing module 170 with all internal components thereof can be located on a common circuit board. The sensing module 170 according to the invention is removably disposed within the wearable article, wherein at least a portion of the sensing module 170 is configured to be in contact with the infant's skin at a location capable of transmitting heart rate. In alternate embodiments, the sensing module 170 further comprises of a microphone 180.

In one embodiment, the sensing module 170 is disposed within the sock such that the sensing module 170 is primarily located around the ankle of an infant. Placing the sensing module 170 around the ankle of the infant may have the benefits of providing greater security to the sensing module. For example, placing the sensing module 170 around the infant's ankle may make it more difficult for the infant to kick the sensing module off. However, one will understand that in at least one embodiment, the sensing module 170 can be placed such that the module is not on the infant's ankle.

The heart-rate sensor 150 according to the invention is configured to record and provide output data corresponding to heart rate of the infant wearing the infant monitoring device. The heart rate sensor provides the raw output data that allows determination of the infant's heart rate. The heart rate sensor 150 as illustrated in FIGS. 1 and 2 is a part of the sensing module 170. The heart-rate sensor 150 is positioned in the sensing module 170 such that a portion of sensor 150 is in sufficient contact with an infant's skin at a location capable of transmitting heart rate. In an embodiment of the invention, the hear-rate sensor 150 records the heart rate of the infant. The heart-rate sensor of the present invention records the heart rate of the infant every 3-5 seconds. In an embodiment of the invention, the heart rate sensor of the invention records the heart rate every 3 seconds.

The heart rate sensor 150 may be one of a relatively large number of heart rate sensors that can detect various different physiological parameters of an infant that can be used to calculate the heart rate. For example, the heart rate may be calculated using one of the following signals: an electrical signal from the infant; an acoustic signal from the infant; a vibration signal from the infant; a blood flow measurement from the infant or a baby's body color or body temperature. In an embodiment of the invention, the heart rate sensor could be a heartbeat waveform sensor. The heart rate sensor then transmits the received signal or the raw data to the microcontroller 100 which in turn transmits it to the computing device application to determine the heart rate value.

The microcontroller 100 of the present invention receives the output or raw data from the heart rate sensor 150, wherein the output data provides information about the infant's heart rate. The microcontroller 100 as illustrated in FIGS. 1 and 2 is a part of the sensing module 170. The microcontroller 100 of the present invention comprises means for processing heart-rate data on-site. Alternatively, the microcontroller 100 can reformat the raw data into a compressed form and provide the compressed raw data to the BLE module 110, which data may be transmitted to the computer device application of a user. In a preferred embodiment of the invention, the microcontroller transmits the raw data to the computing device application for processing the information. The microcontroller 100 can include all necessary means for processing the raw data and relaying that data into a format that can be transmitted through the BLE module 110. The microcontroller is able to transmit heart rate data every 3-5 seconds. In an embodiment of the invention, the microcontroller of the invention transmits heart rate data every 3 seconds.

The microcontroller 100 according to the invention is an Arduino® microcontroller. Arduino® programmable microcontrollers are known in the prior art are open-source electronics prototyping platform. There are other devices available in the market that may be used as an alternative to the Arduino microcontroller, for example, a microcontroller equipped with an ARM Cortex-MO processor, ARM Cortex-M3 processor, ARM Cortex-M4 processor or similarly capable microcontrollers. Such alternate devices are covered under the definition of microcontroller of the present invention.

A BLE module 110 according to the invention refers to Bluetooth Low Energy module that can connect with a Bluetooth host (as iOS device, Android phone, PC etc.). BLE module 110 establishes a connection from the infant monitor to the primary user's computing device such as a phone, computer, or tablet. Through this BLE connection, data from the infant monitor is transmitted to the user of the computing device application. BLE module does not need an internet Wi-Fi connection. As long as the primary user is within the BLE range, the BLE module 110 transmits the heart rate date to the primary user who is able to upload the information to a cloud server. In an embodiment of the present invention, the BLE module 110 transmits heart rate date from the microcontroller to the user phone in real-time. In other words, a new heart rate data is recorded and transmitted by the BLE module 110 in real-time every 3-5 seconds. In an embodiment of the invention, the heart rate data is transmitted in real-time every 3 seconds.

The BLE module 110 has a Bluetooth range of the infant monitor is 50-100 feet. In an embodiment of the present invention, the Bluetooth range is 50 feet. It is understandable that with newer BLE technological advances, the range of the Bluetooth might increase to greater than 50 to 100 feet.

A vibration motor 140 according to the invention, as illustrated in FIGS. 1 and 2, is a part of the sensing module. The vibration motor can be used to wake the baby when a negative health trend is detected. The vibration motor 140 can also be used to stimulate breathing within the baby when a negative trend is detected. In an implementation of the present invention, when an alarming heart rate is detected by the computing device application, the application sends instructions to the infant monitor to trigger a response in the vibration motor 140. The response causes the vibrational motor 140 to vibrate, so as to wake or stimulate the infant. The vibrational motor 140 may be silenced by the user either mechanically or through the computer device application. The vibration motor 140 may also be customized to vibrate at other instances.

A microphone 180 according to the invention transmits the noise of the surrounding environment to the microcontroller 100. As illustrated in FIGS. 1 and 2, the microphone 180 is a part of the sensing module. The microphone 180 according to the invention also records the baseline noise of the infant's surroundings. The microcontroller 100 receives the recorded data and in turn processes the real-time noise data or transmits the raw data to the computing device application. The computing device application compares the recorded noise in real time with the pre-recorded baseline noise date. Based on this data, the computing device application is able to detect attention-requiring instances and ultimately notify the user(s). In various implementations of the present invention, the microphone 180 effectively helps in identifying various types of attention-requiring instances such as when the baby is crying, when there is noise disturbing the sleep of the baby etc.

The computing device application 120 of the present invention is an application that receives the data from the infant monitor. The computer device application 120 is an application related to the infant monitoring device of the present invention that may be installed on the phone or a computing device of the user. The computing device application 120 is the means with which the infant monitor communicates with the user about the baby's heart rate. More specifically, the BLE module of the infant monitor transmits the heart rate data of the infant to the computing device application 120. The computing device application 120 processes the heart rate data received from the infant monitor as real-time heart rate values, and detects any alarming heart rates, or any attention-requiring instances. The heart rate readings processed by the computer device application are accurate to within ±4 BPM. The computing device application 120 uploads the heart rate data using cloud technologies—the data is stored on cloud servers and any user who has the phone application and is connected to the profile of the infant retrieves data from the cloud which then triggers an alert/notification in the respective user's phone. The computing device application 120 will identify and notify the user when the sensing module 170 is running low on battery 160, or if the Bluetooth signal is weak, or any other functions that relate to the operation of the present invention. The computer device application 120 alerts the user within 3 seconds when the Bluetooth connection to the infant monitor is lost or disconnected. The computer device application may also track any false alarm or false attention-requiring instances. Historical data on false alarms may be used to customize the infant monitor to better monitor the infant.

The computing device application 120 of the present invention displays the interpretations of the data received from the sensing module 170. The computing device application has the ability to retrieve historical data from the cloud based servers and compile the data to make informative charts or trends. For example, the computing device application 120 can show a graph tracking the heart-rate of an infant overtime. For example, the computing device application 120 can display an average heart-rate for the past hour. In general, the computing device application 120 can be customized by the "controlling user"—a user that has administrative access to display the processed data in myriad of different ways and also be customized to notify the other "non-controlling user(s)" by setting to desired heart-rate ranges of alert. The controlling users can grant access to one or more non-controlling users or temporary third party users.

The computing device application 120 of the present invention is a software service that allows the data to be stored on the cloud, aggregated, analyzed and allows users to control the notification settings and profile settings of the infant. In an implementation of the present invention, the computing device application 120 can detect alarming heart rate in the infant based on the output received from the microcontroller 100. In an implementation of the present invention, the computing device application detects an alarming heart rate when the heart rate determined by the application is outside a pre-customized heart rate range. Once an alarming heart rate is detected, the computing device application immediately notifies all users of the monitoring device via a push notification on their phone application. In a further embodiment, if an alarming heart rate is detected, the computing device application alerts the microcontroller to trigger a response on the vibrational motor 140.

The computing device application 120 of the present invention can detect an "attention-requiring instance" based on the output received from the microcontroller. The microcontroller in turn receives the information from the microphone recording. In an implementation of the present invention, the computing device application detects an attention-requiring instance when the noise output from the environment recorded by microphone 180 is substantially different when compared to a pre-recorded noise baseline. For example, the computing device application creates an attention-requiring instance when the baby is crying or when the surrounding atmosphere is too noisy for the baby to sleep. Once an attention-requiring instance is detected, the computing device application immediately notifies all users of the monitoring device about the event, via a push notification on their phone application. The application transmits the heart rate data and notifications regarding any alarming heart rate or attention-requiring instances in real time or as customized by the user on the computing device application.

In an embodiment of the present invention, the computing device application 120 allows for customization of the normal heart rate range. For example, a newborn pulse is normally 120-160 beats per minute. In a vulnerable infant, the parent or controlling user may want to be alerted when the heart rate is more than 155, even though such a value may be considered normal. The present invention, allows for customizing the normal heart rate range to 120-155. Such a customization using the computing device application 120, allows the application to detect the heart rate of, for example, 158 as alarming, which then notifies all users, such as the infant's parents, of said reading.

The computing device application 120 of the invention uses cloud technologies for uploading and storing heart rate data of the infant. In an implementation of the present invention, the BLE module of the infant monitor transmits the heart rate data to the computing device application of the primary user, which data is then uploaded to the cloud. The data stored on the cloud may be retrieved or downloaded by any user who has the computing device application of the present invention, has a working internet connection, and who is connected to the profile of said infant. In an embodiment of the invention, all the users of the infant monitor, although they are not on the same wireless network will get notification from the cloud according to their specified notification settings.

In yet another embodiment, the sensing module 170 of the present invention further comprises at least one power source, such as a battery 160 that can power the sensing module 170. The battery 160 can be removable and/or rechargeable.

The sensing module 170 further comprises a visual indicator 190 that indicates when the battery 160 is low on power and/or needs replacing.

In an embodiment of the invention, the wearable infant monitoring device comprises a sensing module 170 removably disposed within a wearable article, wherein at least a portion of the sensing module 170 is configured to be in contact with the infant's skin at a location capable of recording and transmitting heart rate; the sensing module 170 comprising: a) a heart rate sensor 150 configured to provide output data corresponding to heart rate of the infant wearing the infant monitoring device; b) a microcontroller 100 configured to receive or process readings received from the heart rate sensor; c) a vibration motor 140 configured to vibrate whenever the heart rate of the infant falls below a customized range; d) a BLE module 110 in operational unity with the microcontroller that transmits heart rate data to a user on an individual computing device application 120, which computing device application is configured to determine the heart rate value; wherein the BLE module 110 sends the readings to the user computing device application 120 without an intermediary transmitting unit.

In a preferred embodiment of the invention, the wearable infant monitoring device comprising: a sensing module 170 removably disposed within a wearable article, wherein at least a portion of the sensing module 170 is configured to be in contact with the infant's skin at a location capable of recording and transmitting heart rate; the sensing module 170 comprising: a) a heart rate sensor 150 configured to provide output data corresponding to heart rate of the infant wearing the infant monitoring device; b) an Arduino® microcontroller 100 configured to receive or process readings received from the heart rate sensor to determine the infant's heart rate; c) a vibration motor 140 configured to vibrate whenever the heart rate of the infant falls below a customized range; d) a BLE module 110 in operational unity with the microcontroller that transmits heart rate data to a user on an individual computing device application 120; e) a computing device application that is configured to receive and process the data to generate the heart rate of the infant; wherein the BLE module 110 sends the readings to the user computing device application 120 without an intermediary transmitting unit.

In a further embodiment of the above invention, the wearable infant monitoring device comprises a microphone 180 configured to record the noise of the environment around the baby; wherein the BLE module 110 sends the readings to the user computing device application 120 without an intermediary transmitting unit.

In a further embodiment, the infant monitoring device of the present invention comprises a visual indicator 190 configured to display when the battery 160 is low on power. The monitoring device may have alternate indicators such as a beeper or additional vibrator to alert the use of the low batter and/or low Bluetooth signal with the primary user.

In an embodiment of the present invention, the method of monitoring an infant heart rate using the wearable infant monitoring device as described above, comprises of the heart rate sensor 150 collecting output data, wherein the output data provides information about the infant's heart rate; the microcontroller 100 receiving or processing the output data; the BLE module 110 transmitting the output data directly to a user computing device application.

In a preferred embodiment of the above method of monitoring an infant heart rate, the microcontroller 100 transmitting the output data to the computer device application is an Arduino® microcontroller 100.

In a further embodiment of the present invention, method of monitoring the infant heart rate comprises the computer device application detecting an alarming heart rate; the application sending a notification to users connected to the child's profile or are in the network of the application regarding the alarming heart rate; wherein the alarming heart rate is any heart rate value that is lower than a pre-customized heart rate range. The pre-customized heart rate range of the invention is the range entered by the user into the computer device application 120. In a further embodiment, the method comprises of the computing device application triggering a response on the vibrational motor 140; the vibrational motor 140 vibrating until silenced by the user.

In another embodiment of the present invention, the method of monitoring the infant heart rate comprises the microphone 180 recording output related to noise environment from the infant surroundings; the microcontroller 100 receiving and transmitting the output related to noise environment to the computer device application. The computing device application detecting a possible attention-requiring instance; the application sending a notification to users on the computing device application 120 or in the network of the child's profile regarding the attention-requiring instance;

wherein an attention-requiring instance is the instance where the output related to the noise environment is substantially different when compared to a pre-recorded baseline noise environment.

In an embodiment of the present invention, the method of monitoring the infant heart rate and sending all relevant sensor data to the computing device is possible outside the confines of the home as long as there is an established Bluetooth connection to the computing device (phone) of the primary user. The notifications to the other users will be send through the cloud server if and when the primary user gets access to internet. The method comprises of measuring the heart rate outside an internet-free area as long as the primary user of the infant monitor is in the Bluetooth range of 50-100 feet from the infant monitor. The method also enables securely transmitting the heart rate from the internet free area to multiple users not in the Bluetooth area as long as the primary user has a data enabled phone. In the same embodiment, the infant monitor also enables the transmission of the heart rate data, as well as other relevant sensor data, from the internet free area to a cloud based server once the primary user of the infant monitor reestablishes internet connection via a data enabled phone.

In an embodiment of the invention, the method of monitoring the heart rate of the infant continues in the period between when the Bluetooth connection to the primary user is lost and said connection is reestablished. In this embodiment, the sensing module 170 measures the heart rate of the infant, the microprocessor 100 processes the heart rate and determines the heart rate value. If and when the measured heart rate value falls outside the customized heart rate range, the vibration motor 140 is triggered to vibrate to wake up the baby. In the same embodiment, the data from the sensing module is transferred to the computing device application of the primary user when the Bluetooth connection is reestablished.

While the invention has been described above with reference to specific embodiments thereof, it is apparent that many changes, modifications, and variations can be made without departing from the inventive concept disclosed herein, and such description is not intended as limitations on the scope thereof. Accordingly, it is intended to embrace all such changes, modifications, and variations that fall within the spirit and broad scope of the appended claims.

The invention claimed is:

1. A method of monitoring an infant's heart rate using a wearable infant sock, wherein said wearable infant sock comprises a sensing module, said sensing module further comprising a heart rate sensor, a microcontroller, a vibration motor, a BLE module, a computing device application;
said method comprising the following steps:
 (a) the heart rate sensor collecting heart rate data of the infant;
 (b) the microcontroller receiving, and optionally processing the heart rate data from the heart rate sensor;
 (c) the BLE module coordinating with the microcontroller and transmitting the heart rate data to the computing device application of a primary user;
 (d) said computing device application receiving and processing the heart rate data and generating a heart rate value;
 (e) the computing device application detecting an alarming heart rate and sending a notification to the user regarding the alarming heart rate;
 (g) the vibration motor vibrating whenever the heart rate of the infant falls below a customized range;
 wherein the heart rate data is output corresponding to the heart rate of the infant wearing the infant monitoring device;
 wherein the alarming heart rate is any heart rate value that falls outside the customized range;
 wherein the customized heart rate range may be entered by a controlling user into the computer device application;
 wherein the BLE module sends the heart rate data to the user computing device application without an intermediary transmitting unit.

2. The method of claim 1, wherein the infant sock further comprises a microphone; wherein the microphone records noise in environment around the infant.

3. The method of claim 2, further comprising:
 the microphone recording the noise in environment around the infant to generate output;
 the microcontroller receiving and transmitting the output related to the noise of the environment to the computing device application of a primary user;
 the computing device application of the primary user detecting a possible attention-requiring instance;
 the computing device application notifying other users regarding the attention-requiring instance;
 wherein an attention-requiring instance is the instance where the output related to the noise in the environment is substantially different when compared to a pre-recorded baseline noise environment.

4. The method of claim 1, of claim 1, wherein the sensing module further comprises a visual indicator configured to display when battery is low on power.

5. The method of claim 1, further comprising notifying other users of said infant monitor of the heart rate data, wherein said notifying comprises:
 the computing device application of the primary user uploading the heart rate data to a cloud server;
 the other users of said infant monitor downloading the heart rate data on their individual computing device applications.

6. The method of claim 1, further comprising:
 the computing device application sending instructions to microcontroller to trigger a response on the vibration motor; the microcontroller receiving the instruction and triggering a response on the vibration motor;
 the vibration motor vibrating until silenced by the user.

7. The method of claim 1, wherein the BLE module transmits infant heart rate data to the computer device application in real-time; wherein real time comprises transmitting a newly recorded heart rate value every 3-5 seconds.

8. The method of claim 1, wherein the BLE module transmits infant heart rate data to the computer device application in real-time; wherein real time is every 3 seconds.

9. The method of claim 1, wherein the BLE module transmits the heart rate data to the computing device application of the primary user, which application uploads the data on a cloud server, wherein the loaded information is available to be received by other users on their computing device applications.

10. The method of claim 1, wherein the BLE module alerts the user of losing connection with the infant monitor within 3 seconds.

11. The method of claim 1, wherein the heart rate readings are accurate to within ±4 BPM.

12. The method of claim 1, wherein the computer device application stores processed heart rate data.

13. The method of claim 12, wherein the stored data is further processed to identify trends in the heart rate data.

14. The method of claim 1, wherein the heart rate of the infant is measured in an internet free area; said method comprising:
- the BLE module transmitting the heart rate data to the computing device application of the primary user;
- the computing device application of the primary user receiving and processing the output data and generating the heart rate value;
- said computing device application of the primary user uploading the heart rate data to a server upon coming into an internet connected area;
- other users downloading the data from the server.

15. A method of monitoring an infant's heart rate using a wearable infant sock in an internet free area, wherein said wearable infant sock comprises a sensing module, said sensing module further comprising a heart rate sensor, a microcontroller, a vibration motor, a BLE module, a computing device application; said method comprising the following steps:
- (a) the heart rate sensor collecting heart rate data of the infant;
- (b) the microcontroller receiving, optionally processing the heart rate data from the heart rate sensor;
- (c) the BLE module coordinating with the microcontroller and transmitting the heart rate data to the computing device application of a primary user;
- (e) the computing device application of the primary user receiving and processing the output data and generating the heart rate value;
- (e) the computing device application of the primary user detecting an alarming heart rate;
- (g) said computing device application of the primary user uploading the heart rate data to a server upon coming into an internet connected area;
- (h) other users downloading the data from the server;

wherein the heart rate data is output corresponding to the heart rate of the infant wearing the infant monitoring device;

wherein the alarming heart rate is any heart rate value that falls outside a customized range;

wherein the customized heart rate range may be entered by a controlling user into the computer device application;

wherein the BLE module sends the heart rate data to the user computing device application without an intermediary transmitting unit.

* * * * *